United States Patent

Alt

[19]

[11] Patent Number: 6,157,859
[45] Date of Patent: Dec. 5, 2000

[54] UPGRADABLE IMPLANTABLE MEDICAL DEVICE WITH POST-SHOCK PACING AND REDRAW FUNCTIONS

[75] Inventor: Eckhard Alt, Ottobrunn, Germany

[73] Assignee: Sulzer Intermedics, Inc., Angleton, Tex.

[21] Appl. No.: 09/037,168

[22] Filed: Mar. 9, 1998

Related U.S. Application Data

[63] Continuation-in-part of application No. 08/960,560, Oct. 29, 1997, Pat. No. 6,073,049, which is a continuation-in-part of application No. 08/648,707, May 16, 1996, Pat. No. 5,725, 559.

[51] Int. Cl.[7] ...................................................... A61N 1/39
[52] U.S. Cl. ................................................................ 607/4
[58] Field of Search ................................... 607/4, 5, 14, 15

[56] References Cited

U.S. PATENT DOCUMENTS

| | | | |
|---|---|---|---|
| 5,074,301 | 12/1991 | Gilli | 607/5 |
| 5,265,600 | 11/1993 | Adams et al. | 607/4 |
| 5,311,449 | 5/1994 | Adams . | |
| 5,330,509 | 7/1994 | Kroll et al. | 607/14 |
| 5,360,437 | 11/1994 | Thompson . | |
| 5,383,909 | 1/1995 | Keimel . | |
| 5,439,481 | 8/1995 | Adams . | |
| 5,645,569 | 7/1997 | Ayers | 607/4 |
| 5,676,687 | 10/1997 | Ayers | 607/4 |

Primary Examiner—Jeffrey R. Jastrzab
Attorney, Agent, or Firm—Blank Rome Comisky & McCauley LLP

[57] ABSTRACT

An implantable medical interventional device is adapted to provide therapy to a patient in whom the device is implanted to treat cardiac dysrhythmias including tachyarrhythmia. The device performs a plurality of functions corresponding to different levels of therapy for treatment of sensed dysrhythmias, including an electric shock waveform of predetermined energy content for delivery to the patient's heart to terminate at least one type of tachyarrhythmia. In response to cessation of the tachyarrhythmia after delivery of the electric shock waveform, the device promptly thereafter applies post-shock pacing pulses to the heart for a period of time sufficient to allow the heart to recover from the shock and to resume substantially normal sinus rhythm. The device may be upgraded by programming to select among the various functions as necessary to provide designated therapy by suppressing some functions and activating others. The functions include, among others, simulating different conditions of interaction between activity of the heart and the therapies offered by the device, based on stored intrinsic heart beat signals over a respective time period with modified settings of parameters associated with the therapies. The results of the simulated different conditions of interaction can be displayed to show the effectiveness of treatment by the device if the dysrhythmia were actually encountered while the device is programmed with the respective time period and parameter settings.

20 Claims, 4 Drawing Sheets

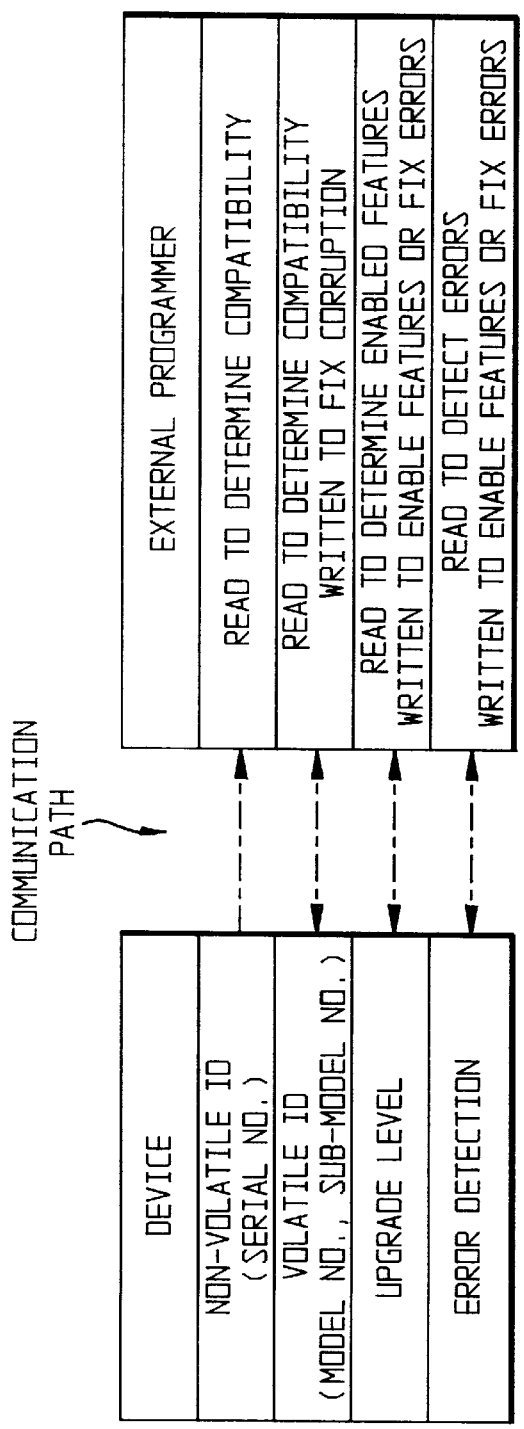
FIG. 2
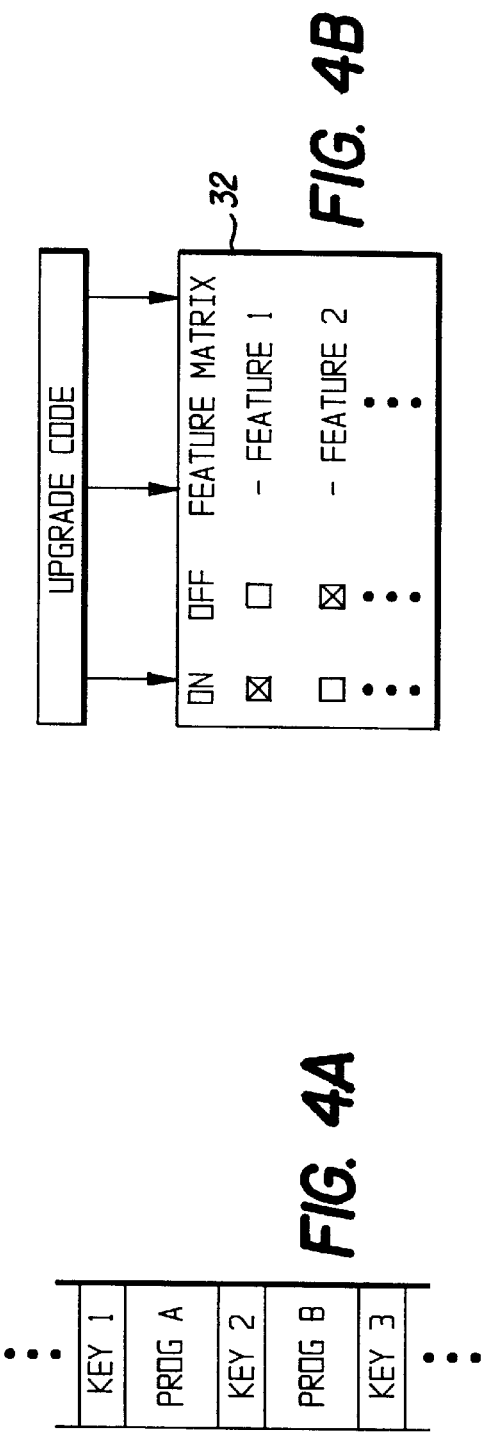
FIG. 4B
FIG. 4A

UPGRADABLE IMPLANTABLE MEDICAL DEVICE WITH POST-SHOCK PACING AND REDRAW FUNCTIONS

CROSS-REFERENCE TO RELATED APPLICATIONS

This application is a continuation-in-part of application Ser. No. 08/960,560, filed Oct. 29, 1997 ("the '560 application" U.S. Pat. No. 6,073,049), which is a continuation-in-part of application Ser. No. 08/648,707 filed on May 16, 1996, which issued Mar. 10, 1998 as U.S. Pat. No. 5,725,559 ("the '559 patent"), both of which are assigned to the assignee of the present application.

BACKGROUND OF THE INVENTION

The present invention relates generally to implantable medical devices for treating cardiac dysrhythmias, and more particularly to a device which is both upgradable by programming to treat dysrhythmias according to a patient's changing needs over time, and responsive to cessation of a shock waveform delivered by the device to the patient's heart to apply post-shock pacing pulses to the affected chamber for a period of time sufficient for the heart to recover to normal heart rate.

Selection of an appropriate pacemaker to be implanted, for example, is made after patient evaluation, diagnosis of the disorder (e.g., dysrhythmia), and determination that artificial pacing can be an effective therapy to alleviate the dysrhythmia. As with any therapy, consideration of side effects and contraindications is vital. Techniques of selecting the respective proper pacing modes for treating particular dysrhythmias are set out in algorithmic form; for example, in M. Schaldach, *Electrotherapy of the heart,* Springer-Verlag, Berlin (1992).

The '559 patent and the '560 application describe multi-mode (pacing, cardioverting, defibrillating) devices implemented with a full range of features which are not all required to be operational at the time of implantation, and which may be upgraded or modified non-invasively while surgically implanted, whenever the progress of the patient's underlying disease or deficiency dictates, through remote programming. For many patients, progression of cardiac disease or disorder has necessitated surgical removal (explantation) of a now less-effective or ineffective device, and implantation of a new device capable of effective treatment of the current dysrhythmia.

U.S. Pat. No. 5,609,613 ("the '613 patent"), commonly assigned herewith, discloses improvements in artificial pacing for various conditions of patient rest, exercise/activity, and atrial dysrhythmia, with enablement of automatic mode switching between dual-chamber and single-chamber modes. The advent of a fully automatic DDD pacemaker allowed adapting the ventricular pacing rate to depend on rate of the sensed intrinsic atrial signal, and AV synchrony. But about 50% of the DDD pacemaker implant patients were found to experience atrial sensing problems or atrial instability, with underlying atrial rhythm disorders, and these patients had to be switched from DDD pacing mode to the simpler VVI mode by pacemaker replacement. Subsequent improvements in sense amplifiers, electrodes for atrial leads, and timing cycles (e.g., dynamic AV delay and refractory periods) enabled DDD pacers to provide effective therapy to some of this patient population, but a considerable percentage of patients with dual chamber implants were still found to have inadequate atrial rates. Some one-third of patients with sick sinus syndrome (characterized by sinoatrial (SA) arrest or SA exit block) exhibit overly high atrial rates and accompanying atrial fibrillation, atrial flutter, or sinus tachycardias including atrial reentry tachycardias and ectopic tachycardiac events (which develop from a focus other than the SA node), as well as slow heart rates.

Rate-adaptive pacing techniques are used to monitor artificial pacing rate and intrinsic heart rate, and for controlling the pacing rate to meet the patient's metabolic needs. For example, the RELAY (a trademark of Sulzer Intermedics Inc.) dual-chamber, multi-programmable, accelerometer-based rate-adaptive cardiac pulse generator not only varies the pacing rate according to the patient's level of activity (or lack of activity, i.e., resting) and body position but also monitors adequacy of triggered pacing of the atrium. In the RELAY™ pacing system, the maximum programmable rate (MPR) is supplemented by a slower interim rate which is greater than the lower rate limit of the device—a ventricular tracking limit (VTL). The pacing rate moves from its base rate to the VTL, conditioned on a high atrial sensed rate without patient exercise. This conditional VTL (CVTL) may be programmed "on" (i.e., as an operating feature of the device) to undergo a controlled jump to the interim rate when a high atrial intrinsic rate is sensed but the accelerometer fails to confirm patient exercise. CVTL is overridden when MPR is programmed "on" and the rate calculated from patient exercise exceeds the programmed base pacing rate by a preselected amount—e.g., 20 beats per minute (bpm). At this accelerometer-based rate threshold, the pacemaker pulse generator restores 1:1 AV synchrony up to the MPR.

The '613 patent discloses a rate-adaptive, dual chamber pacemaker in which the VTL is a dynamic rate, and the ventricular pacing rate is controlled through several different rate zones, based on a combination of (i) dynamic adjustment of VTL according to the accelerometer-based activity signal, and (ii) automatic mode switching from a dual-chamber to a single-chamber mode with reversion to the dual-chamber mode based on an atrial cut-off rate and a programmable rate criterion. Among other things, a mode switch rate (MSR) is designated—above the MPR—that represents an atrial rate unlikely to be exceeded by even a healthy person with a normal cardiovascular system. Mode switching from DDDR to VVIR (the R suffix indicating rate-adaptive functions), for example, may be set to take place automatically when sensed atrial rate exceeds MSR for a programmed number of consecutive cardiac cycles, with reversion to dual-chamber operation occurring automatically when sensed atrial rate falls below MSR for one cycle.

While techniques such as automatic mode switching are highly desirable to avoid a need for physician reprogramming, instances arise in which progression of cardiac disease mandates a more permanent change in device functionality, or additional features not previously required for control of the patient's dysrhythmia. In the '559 patent, an implantable defibrillator is designed to be upgradable non-invasively by selectively programming and re-programming the device in a secure manner each time the patient's condition undergoes a significant change, to provide the minimum functional capabilities required to treat the patient's current dysrhythmia. Various therapeutic features and capabilities of the implanted device which are not required for treating the patient's current disorder may be rendered inactive or disabled for the time being and selectively made available from time to time thereafter when and as prescribed for treatment of an advanced stage of progressive cardiovascular disease, without a requirement of surgical removal and replacement of the implanted device. Initial cost to the patient is relatively low, if applied only to the limited features of the device which have been activated. As additional features are activated in the course of treatment of an advancing disease, additional charges may be imposed to allow recovery of costs of development, manufacture, distribution and marketing associated with those features.

The '560 application discloses an implantable, programmable multi-mode cardiac pacemaker electrical function generator which is adapted to be upgraded selectively and non-invasively, through programming, in a similar manner.

All such programming of functions requires imposition of appropriate security measures, as well as additional charges on the patient's account to compensate the device manufacturer for the extended function(s). To avoid the possibility of unauthorized upgrade, a security code or key supplied by the manufacturer is required to allow the desired mode restoration from a dormant state. Any of several distinct and different security codes which are unique to the particular implanted device may be used for this purpose, or each the security codes may be associated with a respective distinct and different mix of enabled and disabled pacing or functional operating modes, to obtain a particular mix only with a specific one of the codes.

An initially simple and inexpensive device is converted by these means to a more sophisticated device without subjecting the patient to additional surgery. The typical cardiac patient does easily tolerate the physical, mental, emotional, and economic toll of multiple operations which may range from an initial relatively simple implant device to successively more complex devices to meet the advancing needs for therapy dictated by progressive heart disease. Added to this is the care required to be delivered to the patient by physician, surgical, and hospital services, and limited care mandated by government-imposed cost containment especially in the case of patients of advanced years who generally are candidates for such implant devices.

The present invention employs not only the capability to be upgraded by secure programming, but is also directed toward a device having the capability to provide improved diagnostics and therapies to treat tachyarrhythmias. In the majority of cases, tachyarrhythmias are associated with reduced myocardial contractility, where underlying structural disease of the heart is often responsible as well for the occurrence of threatening tachyarrhythmic events. Under normal and usual conditions, treatment with appropriate medication such as ACE inhibitors, digitalis and diuretics can maintain a sufficient cardiac output. But where arrhythmia is present, and especially on occasions following treatment of an arrhythmia, reduced myocardial performance is observed, with severely compromised cardiac output.

Studies conducted by the applicant have shown that VVI pacing with a lack of synchronization of atrial and ventricular activation has a serious adverse effect on myocardial performance in these patients. Normally, an atrial contraction is followed by ventricular activation, which are observed as a P-wave and QRS-complex, respectively, in the ECG, but if the patient is subjected to a defibrillation shock from an implanted device the post-shock rhythms can also severely compromise myocardial performance. The undesirable rhythms result from an alteration of the sinus node induced by the shock(s), and even though the node function may remain adequate with respect to its basic rate, the high energy delivered by the shock has an adverse effect on its chronotropic function. Consequently, ventricular defibrillators tend to reduce the effectiveness of back-up VVI pacing.

These same studies by the applicant have demonstrated that two mechanisms in particular appear to cause reduced cardiac output following delivery of a defibrillation shock. First, the high energy shock itself impacts adversely on the myocardial function, which may be attributable to a type of electroporation that alters the basic contractility. Second, the high energy shock deleteriously affects the chronotropic recovery and the automaticity of the sinus node, which results in considerable lengthening of the phase for depolarization of the atrial natural pacemaker cells. In practice, the atrial rate may fall to values of 30 to 40 beats per minute (bpm), which is much too low in light of the severely compromised myocardial function.

Additionally, in many patients with normal sinus node, a normal conduction in the atrio-ventricular (AV) node is present in antegrade direction, and hence, retrograde conduction from the ventricle to the atrium can occur. Under conditions of VVI pacing, "pacemaker syndrome" is present in which a retrograde activation of the atrium results in cannon waves caused by contraction of the right atrium at a time when the tricuspid valve is closed by contraction of the right ventricle. Consequently, a pumping function of the atrium will lead to a shift of blood in a direction opposite from normal, into the pulmonary veins, rather than toward the right and left ventricle. Conversely, when the mitral valve opens, the atrium is empty which leads to a diminished filling of the ventricle and a resulting serious deficiency in ventricular performance. In practice, these patients exhibit a blood pressure of 60 to 70 millimeters of mercury (mm Hg) during VVI pacing, compared to regular blood pressure of 100 to 110 under conditions of an AV synchronized rhythm such as sinus rhythm or a sequential pacing rhythm following a pacing of the atrium and the ventricle.

It is therefore a principal aim of the present invention to provide an implantable medical interventional device and device-implemented method to improve cardiac output following high energy shocking of the heart by post-shock pacing of the heart for a period sufficient to restore normal sinus rate.

A related aim of the invention is to provide an implantable medical interventional device and device-implemented method which enables temporary post-shock pacing of the atrium and ventricle in treatment of tachyarrhythmias, and wherein the device may be functionally upgraded non-invasively by secure programming.

SUMMARY OF THE INVENTION

According to the invention, an implantable medical interventional device adapted to provide therapy to a patient in whom the device is implanted, to treat cardiac dysrhythmias including tachyarrhythmia, includes means for providing multiple functions corresponding to different levels of therapy for treatment of dysrhythmias, and means responsive to each different type of dysrhythmia sensed by a sensing means associated with the device, for enabling the function providing means to provide a level of therapy appropriate to the respective sensed dysrhythmia including an electric shock waveform of predetermined energy content for delivery to a predetermined chamber of the patient's heart to terminate at least one type of tachyarrhythmia, and means responsive to cessation of the electric shock waveform for promptly thereupon applying post-shock pacing pulses to the atrium for a period of time sufficient to allow the heart to recover from the shock and to resume substantially normal sinus rhythm.

In an embodiment of the device, the period of time of application of post-shock pacing pulses to the atrium preferably exceeds approximately 30 seconds, and most preferably is in a range from approximately 30 seconds to about five minutes. Additionally, the magnitude of the post-shock pacing pulses during the period of application is increased relative to the normal level of pacing pulses supplied by the device The device includes a set of leads electrically coupled thereto, in which a first lead is adapted to be positioned with an electrode in the right atrium of the patient's heart for sensing and pacing cardiac activity of the atrium, a second lead is adapted to be positioned with an electrode in the right ventricle of the patient's heart for sensing and pacing cardiac activity of the ventricle, and a third lead has an electrical coil thereon positioned in the right ventricle for delivering defibrillation shocks to the ventricle relative to the conductive case of the device as an electrode positioned external to the heart.

The detected atrial signals are indicative over time of the atrial ECG morphology, and are stored in memory for subsequent diagnosis of cardiac activity before, during and after a tachyarrhythmic event. To that end, the stored atrial signals representing the patient's atrial ECG morphology are selectively retrieved from the device by telemetry using an external programming console, to facilitate interpretation of cardiac activity leading to and during a tachyarrhythmic event, and the response to therapy delivered by the device subsequent to that event.

Extended memory is also selectively retrievable from dormant functions of the device, for entry of parameters of therapies simulated to treat potential dysrhythmias suffered by the patient, whereby to provide a redraw function by which therapeutic responses of the device to simulated conditions of patient disorders are stored for future application if such disorders are subsequently encountered.

BRIEF DESCRIPTION OF THE DRAWINGS

The above and still further aims, objects, aspects, features and attendant advantages of the present invention will become apparent from a consideration of the following detailed description of the presently contemplated best mode of practicing the invention, by reference to a preferred embodiment and method, taken in conjunction with the accompanying drawings, in which:

FIG. 2 is a chart of characteristics for the device of FIG. 1, and capabilities of an external programmer for accessing and programming memory of the device;

FIGS. 4A, 4B, and 4C are functional block diagrams for explaining an embodiment of the device, and a method of providing therapy using the device;

DETAILED DESCRIPTION OF THE PREFERRED EMBODIMENT AND METHOD OF THE INVENTION

Figure 1:
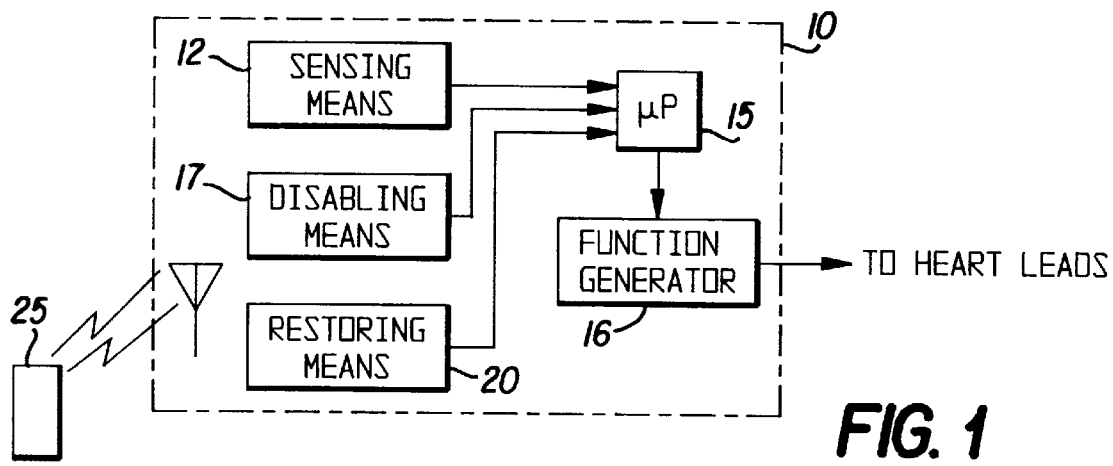
FIG. 1 is a block diagram of an implantable medical interventional device (which includes defibrillating, cardioverting and pacing functions) having programmably upgradable functions described in the '559 patent and the '560 application.

FIG. 1 is a block diagram of an exemplary embodiment of an implantable medical interventional device 10 having capabilities of pacing, cardioversion and defibrillation, such as described in the '559 patent and the '560 application, all of the components of which may be entirely conventional except as otherwise described herein. Device 10 is selectively upgradable by programming from time to time, as necessary or desirable to provide additional therapy for treatment of dysrhythmias of the patient in which the device is implanted, as the patient's need for treatment change with time relative to the treatment programmed at the time of implant or subsequent thereto.

Device 10 includes a function generator 16 for providing a plurality of functions corresponding to different levels of therapy for treatment of dysrhythmias. These may include generating relatively low energy pulse waveforms for pacing therapy including anti-bradycardia and anti-tachycardia pacing, moderate energy cardioverting shock waveforms for cardioversion therapy, and relatively higher energy defibrillating shock waveforms for defibrillation therapy. An output circuit of function generator 16 supplies the designated therapy to a set of leads and electrodes for delivering it to designated chambers of the heart. The output circuit may include capacitors and high voltage switches for producing high energy defibrillating shocks, and the electrodes may include the biocompatible metal housing (i.e., the case, or "can") of device 10 as an active electrode, if desired for a particular type of therapy.

Function generator 16 performs its therapy-generating and delivery functions under the control of a microprocessor 15 containing arithmetic, logic, and control circuitry in conjunction with peripheral circuits or subsystems such as memory, clock, etc., as a central processing unit (CPU) for the device. The microprocessor responds to instructions to perform high speed, real-time functions for controlling the operation of the function generator. The memory units may be written to and read from, by telemetry between device 10 and a program console through a wand 25, and with related software, so that the microprocessor performs desired functions. These functions may then be varied by means of a programming unit, or programmer, by the device manufacturer or the patient's attending physician.

Sensing means 12 in or outside the device housing detects any of various physiologic parameters indicative of the patient's cardiac functions and physical status, to sense dysrhythmias and initiate appropriate response mechanisms from the device. Sensed parameters may include the patient's electrogram (ECG), heart rate and/or rhythm, status of rest, exercise or activity of the patient (e.g., using an accelerometer within the device or in a separate housing), etc., the latter enabling the device 10 to provide a rate adaptive response, as well as other dysrhythmia correction therapies. The sensing means also includes conventional sensors of physiological signals for detecting congestive heart failure, for example.

In response to sensed parameters or signals indicative of a dysrhythmia, the microprocessor-based function generator produces functional output waveforms to correct or otherwise treat the respective sensed dysrhythmia. Some may be used to treat multiple types of arrhythmias. For example, a burst of pulses may be a therapy to terminate a tachycardia, or one among a hierarchy of responses selectively delivered for performing cadioversion. When no immediate demand for therapy is being imposed, the microprocessor reverts to a "sleep" mode, to be awakened at any time a therapy requirement is indicated by the sense signals.

Means 17 are provided for programmably disabling or curtailing at least some of the plurality of functions deliverable from "full-featured" device 10, so that it will address only the needs of the patient at the time of implant. For example, if the patient is experiencing sporadic pathologic tachycardia, but no other cardiac dysrhythmia, the implanted device would be programmed to deliver an anti-tachycardia therapy. This may include, for example, a number of different pulse waveforms (e.g., selectively timed single pulse, pulse train, pulse burst(s)) that are delivered in a hierarchical sequence or regimen ranging from a conservative response to a relatively aggressive response, with suspension of the regimen at any point at which the tachycardia is broken, but restricted to that dysrhythmia. In the event all therapy modes are inadvertently disabled by the programming person, a signal (e.g., audible) is generated by the programmer unit (and/or internally within the implanted pacemaker, e.g., to excite the patient's pectoral muscle) together with a message to that effect on a visual (e.g., liquid crystal) display of the programmer unit, as a warning of the need to correct that situation.

The initial charge to the patient (or third party payor, such as the insurance carrier or the government) for a full-featured device with some of its features programmed to be disabled, would be substantially the same as for a conventional implanted device which is restricted to addressing only the immediate needs of the patient at time of implant, without a capability to be upgraded to other or additional therapy, including charges for the device itself, the surgical procedure, the facility, etc. The difference is that in the latter case, for a patient suffering from a progressive heart disease, implantation of new devices would be required from time to time to treat the advancing cardiac deficiency, with not only the additional costs for the subsequent implants, but trauma and risk to the patient. In contrast, device 10 also includes means 20 for selectively restoring the disabled functions to address the deficiency when and as needed, without a requirement for another surgical procedure and the costs and trauma it entails.

Thus, if upgradable device 10 is implanted, the patient's advancing or progressive needs are readily accommodated by simply programming the implanted device to upgrade its features and functions accordingly. But the selective restoring means includes security means for encoding the device to preclude restoration of disabled functions or other modification of device features except by an authorized entity. This may be implemented so that an upgrade requires participative action by both the attending physician and the device manufacturer.

A full featured implantable medical interventional device includes at least some features that make it a life-saving device, so it should be sufficiently secure to render it virtually incorruptible. To that end, the device has a security system that prevents it from being reprogrammed without an appropriate key or keys. Also, the upgradable device must not be affected by existing applications in the field, to preclude interference or override from existing or future programming or device operation that are or may be available from the device manufacturer. Each upgradable device has its own unique personal identification code, or identifier (ID), which may be embedded in nonvolatile memory of the device to prevent erasure in the event of loss of electrical power to the device.

A compatibility determination check (i.e., to assure compatibility between the upgradable device and the external programmer, particularly with respect to software of each) may be performed by retrieving or verifying the nonvolatile ID (e.g., device serial number), plus a volatile ID (e.g., device model number) which may be embedded in programmable memory to allow it to be changed in the event of corruption. In addition, a data memory of the device has contents identifying the level at which the device is currently upgraded (i.e., the enabled features). Accordingly, the upgrade level may be read at any time by the attending physician to verify the current status of the device; and may be written to in order to reprogram the device to a new upgrade level. An error detection code is provided, which can be read to detect errors, and written to correct errors. These techniques are provided or performed in a conventional manner, the uniqueness residing in the purpose for which they are used.

The device has a backup reset feature that automatically resets to a full-featured device, but that requires programming of the authorized upgrade codes at a later date for all features to remain active. Alternatively, the device is reset to a predetermined limited functional mode, and the user is prompted to obtain upgrade codes from the manufacturer. Both options permit instantaneous restoration of critical feature for patient safety, while preventing unauthorized upgrading of the device.

These capabilities are illustrated, for example, in the chart of FIG. 2. Device characteristics are on the left, external programmer is on the right, and communication direction is illustrated by lines and arrows between the two. All listed characteristics or parameters for the device are stored in read-only memory (ROM) and random access memory (RAM) associated with the device. Device software supports the full range of features available with all combinations of upgrades. The external programmer uses the volatile control parameters of the device software to enable, disable, or limit the range of features according to the selected upgrade level.

Figure 3:
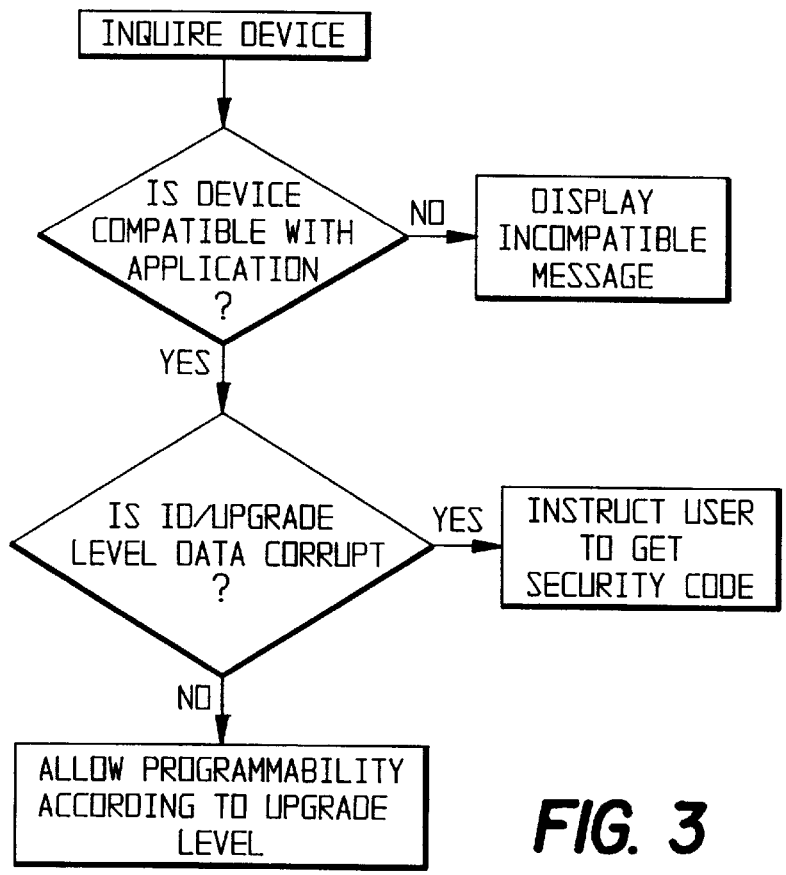
FIG. 3 is a flow diagram for the external programmer application software.

A flow diagram for the external programmer application software is illustrated in FIG. 3. An inquiry to the device from the external programmer (programming console) reads the device ID to determine compatibility of the device with application software of the external programmer. If not compatible, a flag or message is displayed to that effect on a display of the programmer. If compatible, a further test is made to assess corruption of the ID/upgrade level data. If any of the data is corrupt, the user (physician) is instructed to get the security code. Otherwise, the user is notified (also on the display) that programming is permitted to the extent of the upgrade level. Certain features may be limited in range or availability.

FIGS. 4A, B, and C illustrate aspects of external programmer control over features of the device. In FIG. 4A, a security code (e.g., key 1, key 2, key 3, etc.) is required to unlock each program and the feature associated with the respective program. In each instance, the appropriate key (security code) is supplied by the device manufacturer, upon notification from the implant patient's attending physician that the device is to be reprogrammed to modify the original feature or a subsequently upgraded version thereof to meet the patient's current needs for cardiac dysrhythmia therapy. After the key is provided, the modification is made by the physician non-invasively by simply re-programming the implanted device through the external programmer and telemetry. Safeguarding the key assures the manufacturer that it will be notified before any adjustment can be made to the features of the device. A charge may then be imposed for the additional feature(s), or the upgrade, to compensate the device manufacturer for the original implementation. But the cost to the patient is considerably less than that for replacement of the implanted device, without the risk and trauma of a replacement procedure.

FIG. 4B illustrates the status of each feature controlled by the upgrade code, which includes the respective key and the program for that upgrade/feature. For example, feature 1 is programmed "on" while feature 2 is disabled to be "off", and other features are left, restored to be "on" or disabled to be "off" as necessary for the device to meet the current needs of the patient for therapy. A display 32 is provided on the programmer monitor to show the feature matrix as currently programmed.

Figure 4C:
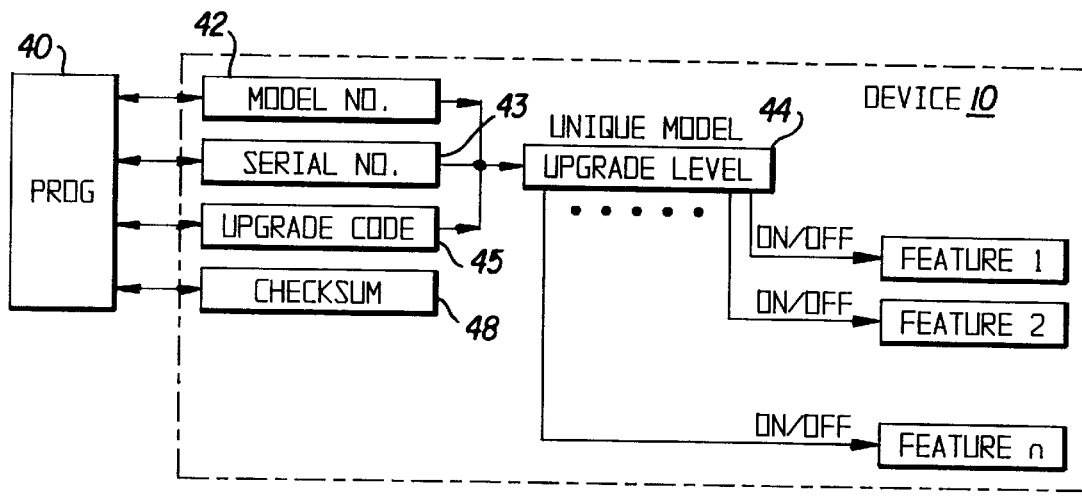

FIG. 4C illustrates interrogation of device 10 by external programmer 40, for model number (at 42) and serial number (at 43). If the response demonstrates positive compatibility, the programmer checks the upgrade level (at 44) of the device and applies an upgrade code (at 46, to manage the availability of certain features defined by sections of the software, by restricting or allowing access with software keys) for installing (restoring) the additional features required according to the patient's condition. A check sum is performed by the programmer (at 48) to detect and correct errors. Having unlocked a feature or features with the applicable key, those unlocked features among 1, 2, . . . N, may be programmed or restored as necessary to provide the features (the prescribed therapies) required to treat the patient's cardiac dysrhythmias.

The upgrade information may be stored in software or semiconductor memory in the device, and is encoded to deter intentional alteration, such as by storing a value which is a complex mathematical combination of the upgrade level, the device model number, and the device serial number. In this way, the upgrade level value stored is unique for each device. The upgrade information, and model and serial number information for the device, are protected by an error detection code such as a checksum, which will allow the application program to recognize alteration or corruption of the serial number or the upgrade level. When an error is detected, the application displays the serial number and upgrade level correction screen on the console, to prompt the user to contact the manufacturer for a security code.

The upgradable device is adapted from an existing conventional device design, with custom programmer software architectures that minimize modifications to existing conventional programmer application code and device code. Programming of each individual function of the device to restore it from a condition in which it had been disabled at the original implantation, imposes a charge to the patient's account. Such charges are imposed as new functions are installed (restored) until the device is made fully operational, i.e., the full range of its features are made available to the patient. Additional charges would apply, for example, to provision of extended memory, VVIR pacing (rate adaptive), VDD pacing, anti-tachycardia pacing, atrial defibrillation, programmable polarity of the shock, programmable impulse characteristics of the shock, and other diagnostic and therapeutic features.

Pacing therapy modes may include combinations of single and dual chamber sensing, pacing, and electrical response functions for treating bradycardia and pathologic tachycardia, as well for providing rate-adaptive pacing using an accelerometer as an activity/exercise sensor. Additionally, the device may be programmed with memory modes and diagnostics that include acquisition of real-time ECG morphology from intracardiac and surface leads, and trends thereof over time, as well as activation of memory or Holter functions in conjunction with various events such as mode switching from DDD to VVI-R pacing when the patient is suffering episodes of atrial fibrillation. The device may be implemented to switch automatically from DDD to VVI pacing mode when a pathologic atrial tachycardia is detected, and to revert automatically from VVI to DDD operation when physiologic atrial tachycardia is sensed, distinct from the pacing therapy modes selected by programming the pacemaker.

The capabilities of the multi-mode programmably upgradable device go well beyond the use of an external programmer to provide data to preselected registers and RAM memory locations within an implanted pacemaker or defibrillator which affect either software routines to be executed or parameters used in that execution. Instead, the programmable upgradability provides a method and system for managing the availability of certain sections of the software constituting operational features of the device, by restricting or allowing access to those features by means of software keys.

The medical interventional device of the present invention provides, in addition to or as a supplemental feature a capability for programmable upgrading, various pacing and post-shock pacing functions that are particularly advantageous in the device arsenal of dysrhythmia treatments. A primary feature of the device resides in providing post-shock pacing of the atrium (and/or ventricle) for a period immediately following delivery of a defibrillation shock (or even a relatively high energy cardioverting shock). The post-shock pacing period should be of sufficient time to allow recovery of the sinus node function from the high energy shock to a resumption of normal sinus rhythm. A period in a range from about 30 seconds to about five minutes has been found to be adequate for this purpose.

Figure 5:
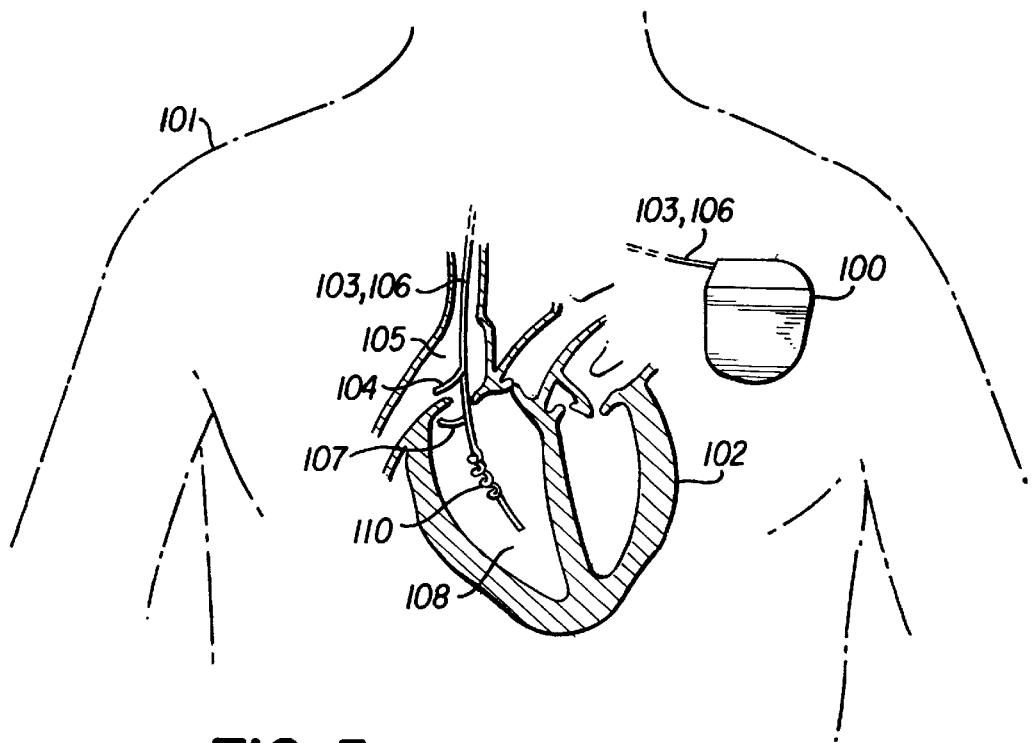
FIG. 5 is a partial front view of a patient depicted in phantom, with a device according to the invention implanted in the left pectoral region of the chest, illustrating the placement of cardiac leads from the device into the patient's heart, and with an external programmer for selectively entering desired functions and therapies into the device and selectively retrieving stored data from the device.

Referring to FIG. 5, device 100 is implanted in the left pectoral region of the chest of a patient 101. The device has connected to it an atrial lead 103 with a bipolar electrode 104 positioned in the right atrium 105 of the heart 102 for sensing and pacing the cardiac activity of the atrium and a ventricular lead 106 with an electrode 107 positioned in the right ventricle 108 beneath the tip of the right atrium for pacing the ventricle and for sensing the underlying ECG. The ventricular lead includes a coil 110 (on a separate lead, albeit in the same sheath) for delivering defibrillation shocks to the ventricles relative to an electrode outside the ventricle. A suitable electrode for this is the metal can that houses the device 100, particularly when the device is implanted in the position noted above.

The device includes a sense amplifier and other means for detecting the atrial ECG morphology for diagnostic purposes, and memory means for storing atrial signals prior to, during and after a tachyarrhythmic event. The ECG morphologies are retrievable later by telemetry from the device, using a program console, to facilitate interpretation of the cardiac activity leading up and at the time of the tachyarrhythmic event of interest, and how the patient's heart responded to the subsequent therapy delivered by the device.

Discrimination between supraventricular tachycardia (originating from outside the ventricle, generally either from the SA node or AV node or the atrium) and ventricular tachycardia is facilitated by a knowledge of the ventricular rhythm and, as well, of the underlying atrial rhythm. If a complete dissociation between the ventricular arrhythmia and the atrial rhythm is found, the diagnosis of ventricular tachycardia would be virtually conclusive. In that case, an anti-tachycardia therapy is delivered by the device and associated lead(s) to the ventricle. However, if the discrimination algorithm determines the atrium to be the primary source of the present tachycardia, the therapeutic intervention would instead be generated and delivered as appropriate to treat a diagnosed primary atrial tachyarrhythmia.

As described in applicant's U.S. Pat. Nos. 4,926,863, 5,014,703 and 5,031,615, for example, commonly assigned herewith, an accelerometer may be used in the device as a sensing means to provide a faithful indication of the status of activity or rest of the patient. This may also be used in determining whether a tachycardia is of supraventricular or ventricular origin.

As pointed out earlier herein, an atrial contraction is normally followed by ventricular activation, observed in the patient's ECG as a P-wave followed by a QRS-complex, respectively. If the patient receives a defibrillation shock from the implanted device, post-shock rhythms erupt which can severely compromise myocardial performance. This is attributable to alteration of the sinus node as a consequence of the shock. The basic rate generated by electrical activity of the node may remain adequate, but the high energy shock can adversely effect the chronotropic function of the node. Consequently, ventricular defibrillators not only tend to reduce the effectiveness of back-up VVI pacing, but can seriously decrease the cardiac output after application of a defibrillation shock. This is true even if the patient normally exhibits no sign of disturbance of the intrinsic pulse formation or pulse conduction, i.e., a normal sinus pulse function and a normal AV conduction. According to current practice, such a patient would be furnished only with a defibrillator with VVI backup pacing.

Mechanisms likely to be responsible for these repercussions of a high energy shock included adverse impact on myocardial function probably due to an electroporation that alters the basic contractility, and on chronotropic recovery and automaticity of the sinus node with concomitant lengthening of the phase for depolarization of the natural pacemaker cells of the atrium. Decline in atrial rate to about 30 to 40 bpm is intolerable where the myocardial function is severely compromised.

Figure 7:
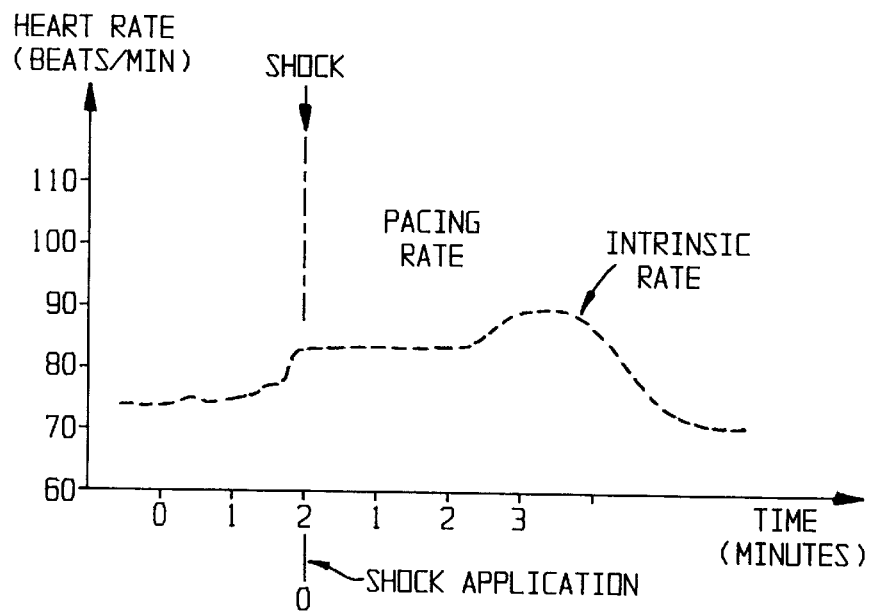
FIG. 7 is a chart illustrating limited post-shock pacing of the atrium (and ventricle, if necessary) for a limited period of time.

To combat these problems, the device of the invention provides post-shock pacing of the atrium (and ventricle, if necessary), commencing with the end of the shock waveform and for a period of time sufficient to allow recovery of the complete sinus node function, which will result in a resumption of normal sinus rhythm. This is shown in FIG. 7. The post-shock pacing is maintained for a period of from about 30 seconds to about five minutes, using the atrial lead 103 and electrode 104 (and, if necessary, the ventricular lead 106 and electrode 107, as with DDD pacing) of device 100 to deliver the post-shock pacing pulses from the function generator.

In addition, because the pacing threshold increases following shock delivery and coincident with the suppression of automaticity, the post-shock atrial (and ventricular) pacing is conducted at a higher energy level than that used for normal pacing stimuli, at least sufficient to exceed the this higher threshold. This may be accomplished by simply programming the device to increase the pacing pulse amplitude during the designated post-shock interval, and then returning to the normal pacing level for any subsequent call-up of a pacing function.

Programmed upgrading of the device enables a full range of pacing to be provided, including anti-bradycardia and anti-tachycardia, with or without full time DDD pacing, as well as rate adaptive functions by employing an accelerometer; and the functions of cardioversion and defibrillation, and of algorithms to discriminate between atrial and ventricular tachycardias (including which chamber is the primary source of the present tachycardia). Thus, the device, by means of programmed downloading, has the capability to address the needs of each patient, including changing needs as they may arise in the course of progression of cardiovascular disease. But as in the case of the devices described in the '559 patent and the '560 application, this is subject to applicable criteria and considerations of physician oversight, prescription and programming; appropriate device security; and financial compensation to the device manufacturer. Use of an accelerometer as an activity sensor in the manner described in the applicant's '863, 703 and '615 patents cited above, allows the device to perform rate adaptive pacing (from VVI to VVIR, or from DDD to DDDR, for example), as well as discrimination between pathologic and physiologic tachycardias, and between tachycardias of supraventricular and ventricular origin, by the programmed non-invasive upgrading of the device.

Extended memory may also be made available in the device, but disabled at the time of implant. The extended memory can be provided later, for example, for purposes of a redraw function of the device. In essence, this function allows the features and functions of the device to be optimized according to a prognosis of the patient's needs at some time during the course of progressive cardiac disease. These needs are directed to target points by which to simulate device response. If the simulation demonstrates a desired effect, the parameters which led to that effect are adjusted to reflect the simulation, which will be repeated as an actual response of the device when the dysrhythmia for which the simulation was done is encountered in future. In essence, the rate response of the device is optimally tailored by precise fine tuning to treat a specific disorder for a particular patient. Frequency and rate of occurrence of atrial and ventricular pacing, or rate profile, including the redraw function, are added to the device operational functions to provide a history—which may include simulated response of the device to certain cardiac events for the specific individual patient in which the device is or is to be implanted.

The redraw function may encompass actual or simulated pacing rate activity during a variable time frame of preselected duration from only a few minutes to several weeks. As part of the memory or extended memory function, the heart rate and pacing rate as monitored (or simulated) are stored and the pacing rate is displayed, the pacing rate display being indicative, for example, of the device response with a currently programmed setting of a rate adaptive function. This constitutes means for simulating different conditions of the device and heart interaction on the basis of stored intrinsic heart beat signals over a respective time period with modified device settings. These results are then displayed on a monitor screen or on a hard (paper) copy in the form of an X/Y graph representing the respective parameter along the Y-axis and the time scale along the X-axis (the redraw function). The parameters may then be varied among the plurality of different ones from which to choose, and the time scale may be varied from minutes, to hours, to days.

The redraw function thereby enables demonstration of simulated heart rate and pacing rate interventions for different settings of the characteristics of the device (e.g., pacemaker, or pacemaker functions of a multi-mode device) programming. The redraw function can do the same with respect to characteristics of portions of the device such as the activity sensor (e.g., an accelerometer) that trigger the rate adaptive response of the device. Redraw itself is known, and in use, for example, in various types of bradycardia and other pacemakers.

Figure 6:
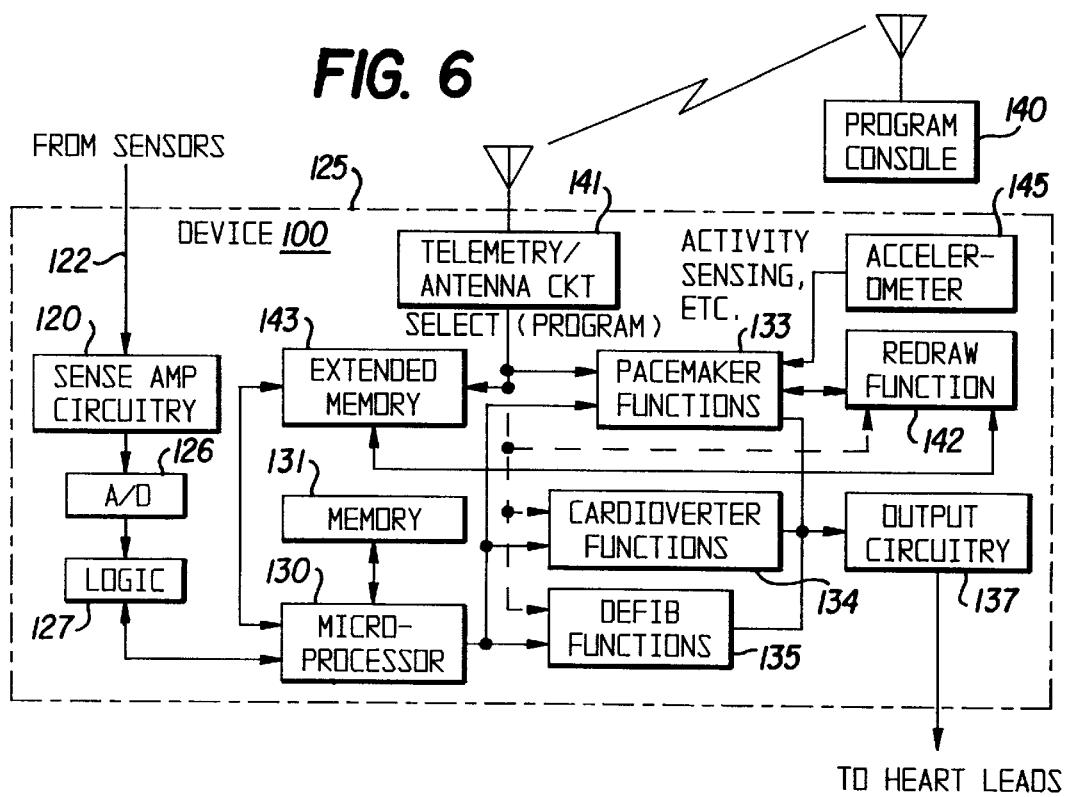
FIG. 6 is a block diagram of a portion of the internal circuitry of the device.

Referring to FIG. 6, a more detailed block diagram of the device 100, sense amplifier circuitry 120 responds to analog input signals 122 from sensors (sensing means) which may be both external and internal to the device housing 125. The processed signals from 120 are applied to an A/D converter 126 and the digital output is delivered to logic circuitry 127 which interacts with microprocessor 130 and memory 131 (which includes both program memory and data memory) to process operating instructions for the device. Depending on the nature of the sensed signals, i.e., whether they are indicative of a dysrhythmia (such as a tachyarrhythmia) and, if so, the specific type of dysrhythmia, the device would ordinarily respond with the appropriate pacemaker functions, cardioverter functions or defibrillator functions, as indicated by boxes 133, 134 or 135, respectively, under the control of the microprocessor. The appropriate waveform for the specified therapy to alleviate the dysrhythmia, whether pulses, pulse bursts or trains, or low energy or high energy shocks, is generated by the output circuitry 137 to the applicable heart lead(s) and thence to the heart itself.

Here, the ordinary operation of the device 100 is affected by the programmed designation of disabled and activated functions, however, having been accomplished by telemetry through use of the external program console 140 and telemetry circuitry including antenna 141 in the device. These selections affect whether the various functions, including pacing 133, cardioverting 134 and defibrillating 135, as well as redraw 142, extended memory 143, and, if desired, activity sensing (using accelerometer 145) are currently available for treating the patient, as discussed above.

Although a presently contemplated best mode of practicing the invention has been described herein, it will be recognized by those skilled in the art to which the invention pertains from a consideration of the foregoing description of a presently preferred embodiment, that variations and modifications of this exemplary embodiment and method may be made without departing from the true spirit and scope of the invention. Accordingly, it is intended that the invention shall be limited only by the appended claims and the rules and principles of applicable law.

What is claimed is:

1. An implantable medical interventional device adapted to provide therapy to a patient in whom the device is implanted to treat cardiac dysrhythmias including tachyarrhythmia, said device comprising a therapy function generator for providing a plurality of functions corresponding to different levels of therapy for treatment of sensed dysrhythmias, said functions including an electric shock waveform of predetermined energy content for delivery to the patient's heart to terminate at least one type of sensed tachyarrhythmia; said function generator being responsive to cessation of the tachyarrhythmia following delivery of the electric shock waveform for promptly thereafter applying post-shock pacing pulses to the heart with a magnitude exceeding a predetermined threshold greater than the threshold for normal pacing of the patient's heart by the device, for the duration of a period of time sufficient to allow the heart to recover from the shock and to commence sinus rhythm.

2. The device of claim 1, wherein said period of time of application of post-shock pacing pulses exceeds approximately 30 seconds.

3. The device of claim 1, wherein said period of time of application of post-shock pacing pulses is from approximately 30 seconds to about five minutes.

4. The device of claim 1, further including means for sensing dysrhythmias to be treated, a first lead electrically coupled to said function generator and said sensing means and having an electrode exposed thereon and adapted to be positioned in the right atrium of the patient's heart for sensing and pacing cardiac activity of the atrium; a second lead electrically coupled to said function generator and said sensing means and having an electrode exposed thereon and adapted to be positioned in the right ventricle of the patient's heart for sensing and pacing cardiac activity of the ventricle.

5. The device of claim 4, wherein said device includes an electrically conductive case for housing components of the device including said function generator and said sensing means, and further includes a third lead electrically coupled to said function generator and having an electrical coil thereon for delivering defibrillation shocks to the ventricle relative to said conductive case as an electrode positioned external to the heart, said coil adapted to be positioned in the right ventricle.

6. The device of claim 4, further including:

means for detecting atrial signals indicative over time of the atrial ECG morphology, and memory means for storing said atrial signals, and thereby, the atrial ECG morphology, for diagnosis of cardiac activity before, during and after a tachyarrhythmia.

7. The device of claim 6, further including:

telemetry means for selective retrieval of the stored atrial signals representing the patient's atrial ECG morphology to facilitate interpretation of cardiac activity leading to and during the tachyarrhythmia, and in response to therapy delivered by the device subsequent to detection of such event.

8. An implantable medical interventional device adapted to provide therapy to a patient in whom the device is implanted to treat cardiac dysrhythmias including tachyarrhythmia, said device comprising a therapy function generator for providing a plurality of functions corresponding to different levels of therapy for treatment of sensed dysrhythmias, said functions including an electric shock waveform of predetermined energy content for delivery to the patient's heart to terminate at least one type of sensed tachyarrhythmia; said function generator being responsive to cessation of the tachyarrhythmia following delivery of the electric shock waveform for promptly thereafter applying post-shock pacing pulses to the heart for a period of time sufficient to allow the heart to recover from the shock and to commence sinus rhythm; said function generator further including means for selectively curtailing or restoring at least some of said functions; an extended memory, and means for selectively retrieving from said extended memory a stored therapy function having parameters used for successful treatment of a simulated dysrhythmia suffered by the patient, whereby to provide a redraw function by which said successful therapy function is reusable upon sensing an actual occurrence of said simulated dysrhythmia.

9. Advice-implemented method of treating cardiac dysrhythmias, including tachyarrhythmia, with an implantable medical interventional device adapted to deliver therapy to an implant patient, wherein the device possesses the capability to provide a plurality of functions corresponding to different levels of therapy for treatment of dysrhythmias, said method including the steps of:

sensing any of a plurality of different types of dysrhythmias of the patient's heart;

responding to each different type of sensed dysrhythmia by delivering to the patient's heart a programmed level of therapy appropriate thereto, including, when at least one type of tachyarrhythmia is sensed, delivering an electric shock waveform of predetermined energy content to a selected chamber of the patient's heart to terminate said sensed tachyarrhythmia; and promptly upon cessation of said sensed tachyarrhythmia, ceasing further delivery of the electric shock waveform and instead applying post-shock pacing pulses to the patient's heart with a magnitude exceeding a predetermined threshold greater than the threshold for normal pacing of the patient's heart by the device, for the duration of a period of time sufficient for the heart to recover from the shock and to commence sinus rhythm.

10. The device-implemented method of claim 9, including applying said post-shock pacing pulses to the heart for a period exceeding approximately 30 seconds.

11. The device-implemented method of claim 9, including applying said post-shock pacing pulses to the heart for a period of up to about five minutes.

12. A device-implemented method of treating cardiac dysrhythmias, including tachyarrhythmia, with an implantable medical interventional device adapted to deliver therapy to an implant patient, wherein the device possesses the capability to provide a plurality of functions corresponding to different levels of therapy for treatment of dysrhythmias, said method including the steps of:

sensing any of a plurality of different types of dysrhythmias of the patient's heart;

responding to each different type of sensed dysrhythmia by delivering to the patient's heart a programmed level of therapy appropriate thereto, including, when at least one type of tachyarrhythmia is sensed, delivering an electric shock waveform of predetermined energy content to a selected chamber of the patient's heart to terminate said sensed tachyarrhythmia;

promptly upon cessation of said sensed tachyarrhythmia, ceasing further delivery of the electric shock waveform and instead applying post-shock pacing pulses to the patient's heart for a period of time sufficient for the heart to recover from the shock and to commence sinus rhythm, sensing and, when required, pacing cardiac activity of the atrium via a first lead from the device inserted in the patient's heart with a bipolar electrode of said first lead positioned in the right atrium;

when required, pacing cardiac activity of the ventricle and sensing the underlying ECG via a second lead from the device inserted in the patient's heart with an electrode of said second lead positioned in the right ventricle; and when required, delivering defibrillation shocks to the ventricle via a third lead from the device with an electrical coil of said third lead positioned in the right ventricle relative to an electrode positioned external to the ventricle.

13. The device-implemented method of claim 12, including the step of:

with a therapy function generator of the device implanted in the left pectoral region of the patient's chest, using an electrically conductive case that houses said function generator as said electrode positioned external to the ventricle for delivery of said defibrillation shocks relative to said electrical coil.

14. The device-implemented method of claim 12, including the steps of:

detecting the atrial ECG morphology from said electrode of said first lead when positioned in the right atrial appendage, and storing atrial signals indicative of the detected atrial ECG morphology for diagnosis of cardiac activity before, during and after a tachyarrhythmic event.

15. The device-implemented method of claim 14, including the step of:

selectively retrieving the stored atrial signals representing the patient's atrial ECG morphology by telemetry from the device, to facilitate interpretation of cardiac activity leading to and during a tachyarrhythmic event, and response of the heart to therapy delivered by the device subsequent to detection of such event.

16. A device-implemented method of treating cardiac dysrhythmias, including tachyarrhythmia, with an implantable medical interventional device adapted to deliver therapy to an implant patient, wherein the device possesses the capability to provide a plurality of functions corresponding to different levels of therapy for treatment of dysrhythmias, said method including the steps of:

sensing any of a plurality of different types of dysrhythmias of the patient's heart;

responding to each different type of sensed dysrhythmia by delivering to the patient's heart a programmed level of therapy appropriate thereto, including, when at least one type of tachyarrhythmia is sensed, delivering an electric shock waveform of predetermined energy content to a selected chamber of the patient's heart to terminate said sensed tachyarrhythmia;

promptly upon cessation of said sensed tachyarrhythmia, ceasing further delivery of the electric shock waveform and instead applying post-shock pacing pulses to the patient's heart for a period of time sufficient for the heart to recover from the shock and to commence sinus rhythm, and selectively retrieving from an extended memory of the device a stored therapy function having parameters used for successful treatment of a simulated dysrhythmia suffered by the patient, whereby to provide a redraw function by which said successful therapy function is reusable upon sensing an actual occurrence of said simulated dysrhythmia.

17. An implantable medical interventional device for delivering an appropriate therapy to an implant patient suffering from one or more cardiac dysrhythmias, said device comprising a therapy generator for providing said appropriate therapy from among a plurality of therapies available from said generator in response to a respective sensed dysrhythmia, one said appropriate therapy being an electric shock waveform of relatively high energy content for delivery to a selected chamber of the patient's heart to terminate a tachyarrhythmia thereof; said therapy generator including a portion responsive to cessation of further delivery of said electric shock waveform to the selected chamber upon termination of said tachyarrhythmia for promptly thereupon applying post-shock pacing pulses to said selected chamber for a period of time sufficient to allow the patient's heart to recover from said shock waveform and to commence a sinus rhythm; said device further including a programmable portion for selectively temporarily disabling the availability of any one or more, including said electric shock waveform, but less than all, of said plurality of therapies from said generator.

18. The device of claim 17, further including apparatus for ascertaining that an available one of said plurality of therapies is particularly effective for treating a particular dysrhythmia of the patient's heart, and for initiating said particularly effective therapy whenever said particular dysrhythmia is sensed.

19. The device of claim 17, wherein said programmable portion includes apparatus for selectively restoring the availability of at least one temporarily disabled therapy through a security code.

20. An implantable pacemaker/cardioverter/defibrillator device adapted to be upgraded from time to time to enable the device to provide additional therapy for treatment of dysrhythmias in a patient in whom the device is implanted, as the needs of the patient for such treatment undergo change, said device comprising a therapy function generator for providing a plurality of functions corresponding to different levels of therapy for treatment of dysrhythmias; means for sensing any of a plurality of different types of dysrhythmias; means responsive to each different type of dysrhythmia sensed by said sensing means for enabling said function generator to provide a level of therapy appropriate to the respective sensed dysrhythmia, said plurality of functions including an electric shock waveform of predetermined energy content for delivery to a selected chamber of the patient's heart to terminate a sensed tachyarrhythmia and a waveform containing a plurality of post-shock pacing pulses to be delivered to the heart promptly following termination of said tachyarrhythmia for a period of time sufficient to allow the heart to recover from the shock waveform and to resume substantially normal sinus rhythm; and means for programmably curtailing the availability of at least some of said plurality of functions from said function generator and for selectively restoring the curtailed functions when needed upon access through a security code.

* * * * *